United States Patent [19]

Siczek et al.

[11] Patent Number: 5,014,292
[45] Date of Patent: May 7, 1991

[54] TILTABLE X-RAY TABLE INTEGRATED WITH CARRIAGE FOR X-RAY SOURCE AND RECEPTOR

[76] Inventors: Bernard W. Siczek; Aldona A. Siczek, both of 1252 Chinook Way, Boulder, Colo. 80303

[21] Appl. No.: 471,623
[22] Filed: Jan. 29, 1990
[51] Int. Cl.⁵ .............................................. H05G 1/02
[52] U.S. Cl. ................................... 378/196; 378/195; 378/197; 378/208; 378/209
[58] Field of Search ............... 378/193, 195, 196, 197, 378/198, 204, 205, 208, 209, 38–40, 176–179, 189, 190

[56] References Cited

U.S. PATENT DOCUMENTS

| | | | |
|---|---|---|---|
| 2,534,623 | 12/1950 | Pitts et al. | 378/209 |
| 3,131,301 | 4/1964 | Barrett et al. | 250/55 |
| 3,822,875 | 7/1974 | Schmedemann | 269/323 |
| 4,334,155 | 6/1982 | Gieschen et al. | 378/196 |
| 4,365,345 | 12/1982 | Graig et al. | 378/196 |
| 4,618,133 | 10/1986 | Siczek | 378/209 |
| 4,653,083 | 3/1987 | Rossi | 378/209 |
| 4,841,585 | 6/1989 | Masuzawa | 378/209 |
| 4,842,259 | 6/1989 | Rice | 378/209 |

Primary Examiner—Edward P. Westin
Assistant Examiner—Kim-Kwok Chu

[57] ABSTRACT

An X-ray examination apparatus comprising: a base assembly including a pivotable and vertically displaceable frame, a first actuating means for pivotal movement of said frame about a horizontal axis and a second actuating means for vertical movement of said frame, computer controls for controlling said first and second actuating means individually and in combination, two parallel rail systems supported by the frame and having two carriages mounted respectively thereon, which carriages can move in unison or individually, one of said carriages supporting a C- or U-shaped carriage for supporting an X-ray source and image receptor in a rotatable arrangement about an axis parallel to said horizontal axis and the other of said carriage having an overhanging support secured thereto, which support includes a dual action mechanism for supporting a patient table in an arrangement providing its vertical movement relative to the frame and its pivoting movement about an axis parallel to its longitudinal axis.

7 Claims, 4 Drawing Sheets

TILTABLE X-RAY TABLE INTEGRATED WITH CARRIAGE FOR X-RAY SOURCE AND RECEPTOR

FIELD OF INVENTION

This invention relates to an X-ray apparatus comprising a tiltable table positioner integrated with a carriage assembly supporting an X-ray source and an X-ray receptor (radiographic or flouroscopic) for use in diagnostic examinations and medical treatments.

BACKGROUND OF INVENTION

An X-ray diagnostic apparatus is well known in which a table positioner integrated with a carriage assembly for supporting an X-ray source and an image receptor to effect diagnostic examinations and medical treatment. However, some improvements are desirable to enhance their effective use in a broader range of applications and reduce their size and cost.

One of the most important limitation of the devices according to the prior art is a mechanical linkage of a pivoting means with a translation means precluding maintaining the table elevation at the desired level for best magnification. Another is that the table tops are supported on a floor base restricting access to a patient. Additionally, the prior art did not include a spot device or a film changer tiltable relative to the table top plane.

SUMMARY OF THE INVENTION

The principle object of this invention is to provide a novel and improved an X-ray examination apparatus comprising a table positioner integrated with a carriage assembly for supporting an X-ray source and an image receptor which apparatus offers a great versatility and flexibility of positioning the radiation axis and a patient to enable substantially full coverage of the patient's body and more effective use in a wide range of applications.

Related objects are to provide a simple and compact construction at reduced cost.

One aspect of the invention resides in a novel construction of a support assembly including a floor engaging section and a frame means for supporting the table positioner and the carrier assembly wherein this frame means includes two independent drive means (not linked mechanically as in the prior art) one for pivoting and another one for translating the frame means relative to the floor plane, a control means for controlling these drive means individually or in combination to produce vertical or pivotal or lengthwise angular displacement up to 90° in either direction from a horizontal position.

Another aspect of this invention resides in a suspension of the table top at one end only, providing an unobstructed access to a patient from both sides. And further this suspension includes a pantograph structure for the table top rotation around its longitudinal axis and for adjusting its elevation in any plane (independent of vertical movement of the frame means) to provide versatility in positioning.

Another feature of the invention resides in a two carriage system included in the support assembly, one supporting the carriage assembly and the other table top for relative movement therebetween, each of which traveling only a half of the desired distance.

Still another feature of this invention resides in a construction of a support of the carriage assembly for displacement of the radiation axis relative to a selected portion of a patient's body being examined in three directions generally perpendicular to one another for greater versatility of the apparatus. (A spot device if included as part of the image receptor may be tilted around a transverse axis of the table top.)

Another feature is swiveling of the table top away from the carrier assembly to effectively accommodate loading and unloading of a patient as well as to free space for rotation of the carriage assembly 180° to interchange a position of the X-ray source with that of the image receptor, one being above and the other being below the table top.

THE DRAWINGS

THE PREFERRED EMBODIMENT

Figure 1:
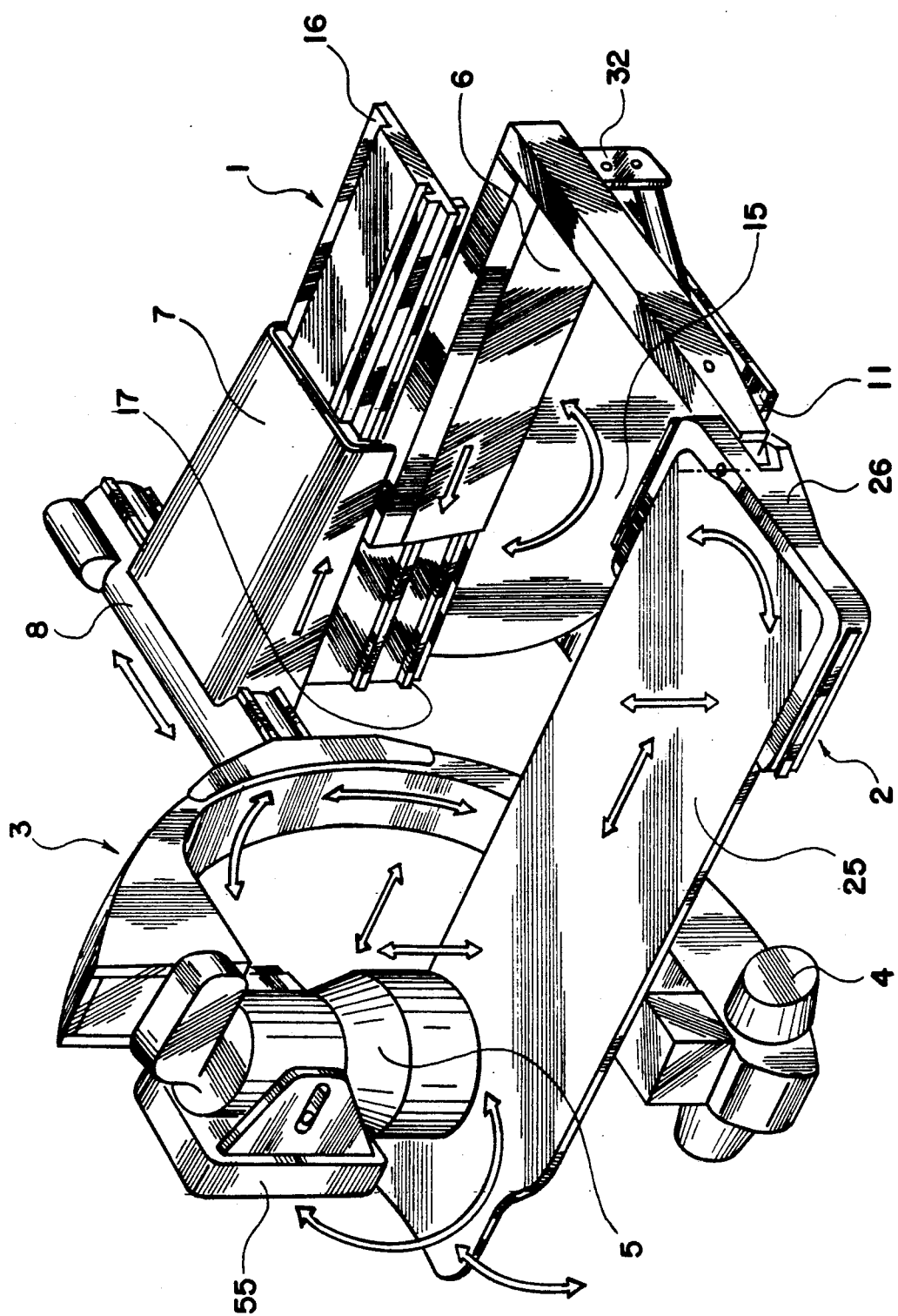
FIG. 1 is an isometric view of the apparatus of the present invention.
Figure 2:
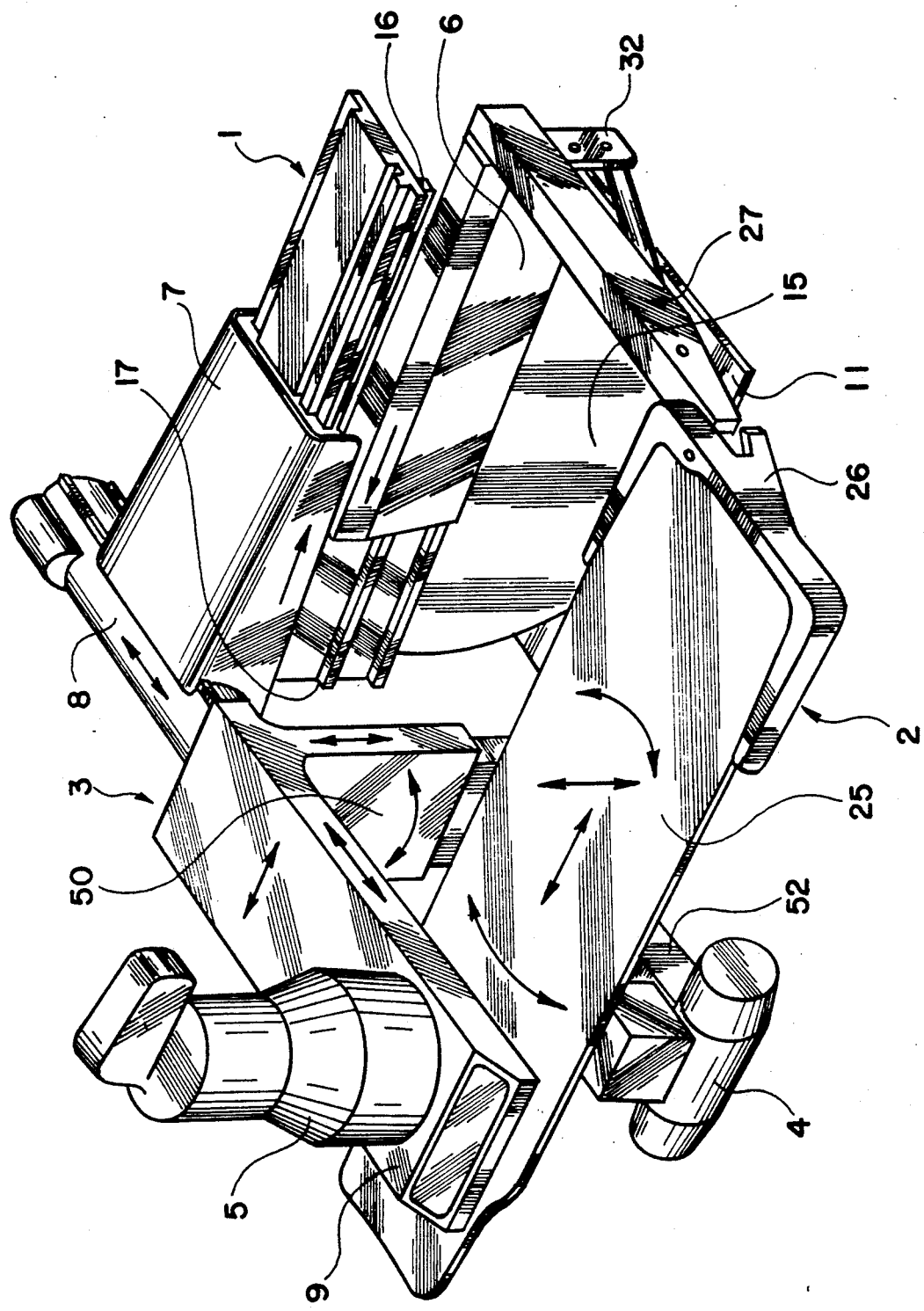
FIG. 2 is an isometric view of an alternative embodiment of the apparatus of the present invention.

An X-ray examination apparatus according to this invention is illustrated in one embodiment in the isometric drawing of FIG. 1 and in an alternative embodiment in the isometric drawing of FIG. 2.

This apparatus comprises a support assembly 1 moveably support a table positioner 2 and a carrier assembly 3 having an X-ray source 4 and an X-ray image receptor 5 defining a common radiation axis mounted thereon in spaced positions for examination of a patient's body positioned on table positioner 2 at a location therebetween so that the radiation axis passes through the body being examined.

Figure 3:
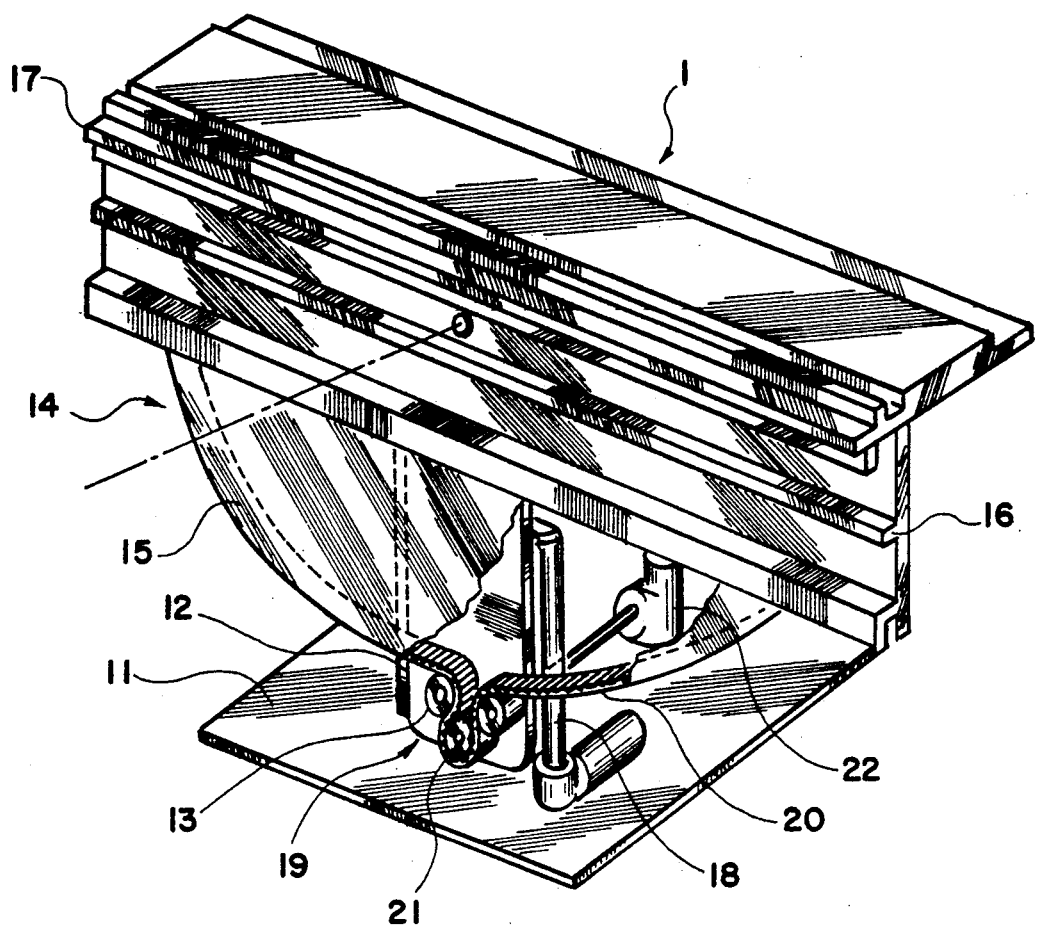
FIG. 3 illustrates the support assembly.

Base assembly 1 (best shown in FIG. 3) comprises: a floor engaging support 11 including a vertically extending support member 12 supporting a vertical member 13 in a sliding relationship in directions parallel to the z axis disposed vertically in the x,y,z coordinate system where the x,y plane is in a horizontal plane; a frame means 14 including a semicircular plate 15 mounted on vertical member 13 in a pivotable arrangement about an axis generally parallel to the y axis, a rail system 16 extending in a direction parallel to the x axis, a rail system 17 parallel to rail system 16, wherein both rail systems 16 and 17 are secured to semicircular plate 15; an actuating means 18 (comprising a ball screw linear actuator) for displacement of vertical member 13 along the z axis, a second actuating means 19 (including a timing belt 20 extending over circumference of semicircular plate 15 and a timing pulley 21 connected to a motor 22) for pivoting frame means 14 a computer control means (not shown) for controlling actuating means 18 and 19 individually and in combination to cause independent or combined movements of the vertical member 13 and the angular displacement of the frame means 14 up to 90° in either direction from the horizontal position.

Table positioner 2 comprises a table top 25 mounted at one end in a frame 26 (extending over a short distance along the sides leaving majority of the table top length metal free and unobstructed) which frame is pivotally secured to a pantograph structure 27 which structure at its other end is moveably secured to a carriage means 6 mounted on rail system 16 in a sliding relationship along the x axis.

Figure 4:
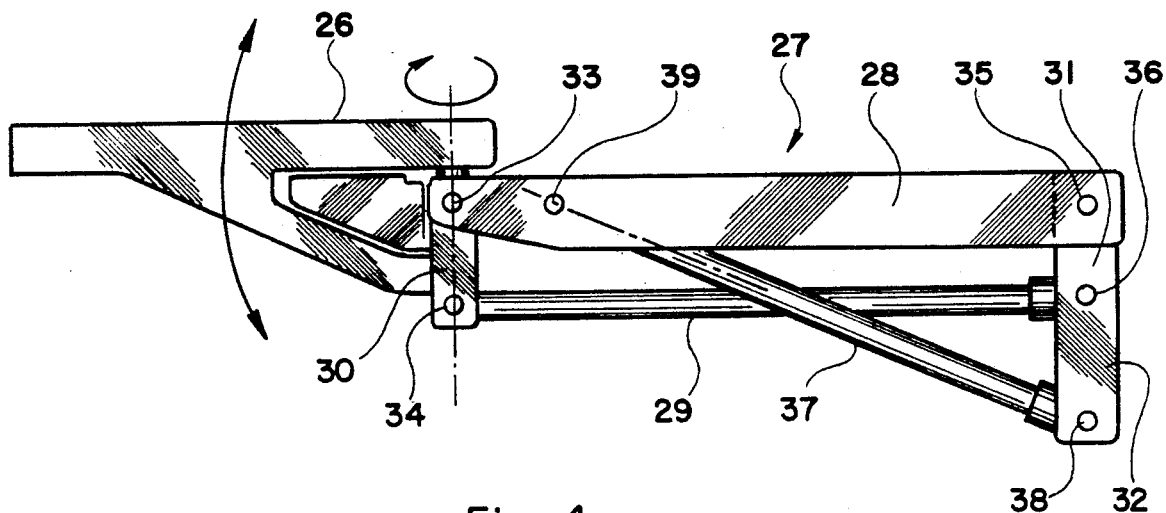
FIG. 4 is a side view and FIG. 5 is a view from beneath the table of the pantograph structure.
Figure 5:
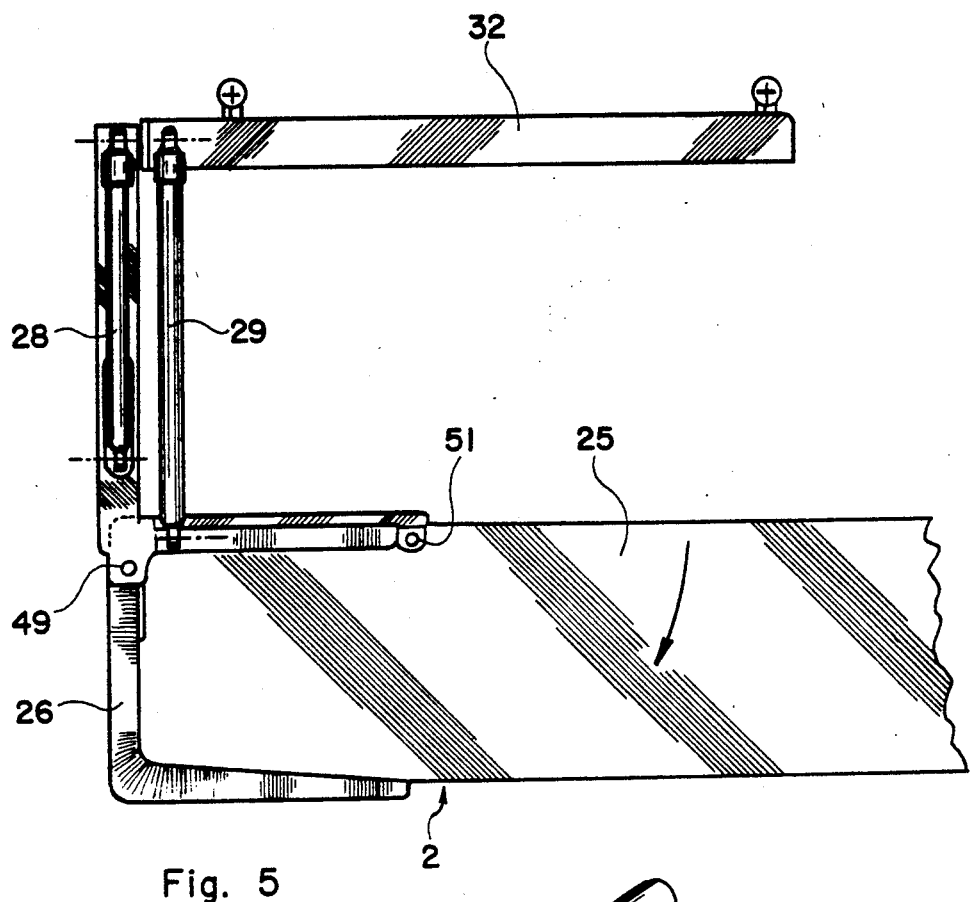

Pantograph structure 27 for adjusting the table top elevation relative to the base 11 and for its rotation about its longitudinal axis comprises (as best shown in a side view in FIG. 4 and a view from beneath the table top in FIG. 5) an overhanging supporting structure including two pairs of parallel arm members 28,29 and 30,31 (wherein arm member 31 is a section of an side end 32 of the carriage means 6) pivotally connected in their respective pivot points 33,34,35,36 wherein arm 29 is of adjustable length (such as a linear actuator) to cause rotation of the table top around its longitudinal axis (cradle motion), which supporting structure also includes a diagonal arm 37 of adjustable length for angular adjustment of the supporting structure, said arm 37 being pivotally supported at one end to side end 32 at the pivot point 38 and at its other end to arm 28 at the pivot point 39.

C-shaped carriage assembly 3 (FIG. 1) is rotatably mounted about an axis parallel to the x axis on an elongated support member 8 which member is mounted on a carriage 7 in a slideable arrangement in directions parallel to the y axis wherein carriage 7 is mounted on rail system 17 in a sliding relationship in directions parallel to the axis. Elongated support member 8 includes a drive assembly for rotating carriage assembly 3 in a vertical or tilted plane passing through a patient's body and around a longitudinal axis of elongated support member 8. Image receptor 5 may be slideable along the radiation axis; a film Puck changer 55 may be mounted on image receptor 5 and displaced from a position beneath said image receptor to a side thereof while not in use. (This is a subject of our application filed on Aug. 25, 1989 No. 07/398,834).

Carriage 6 and carriage 7 at either of their outwardly extreme positions overhang from the two opposite ends of frame means 14 so that the length of rail systems 16 and 17 is smaller than the length of table top 25 and still enabling substantially full coverage of a patient's body.

Figure 6:
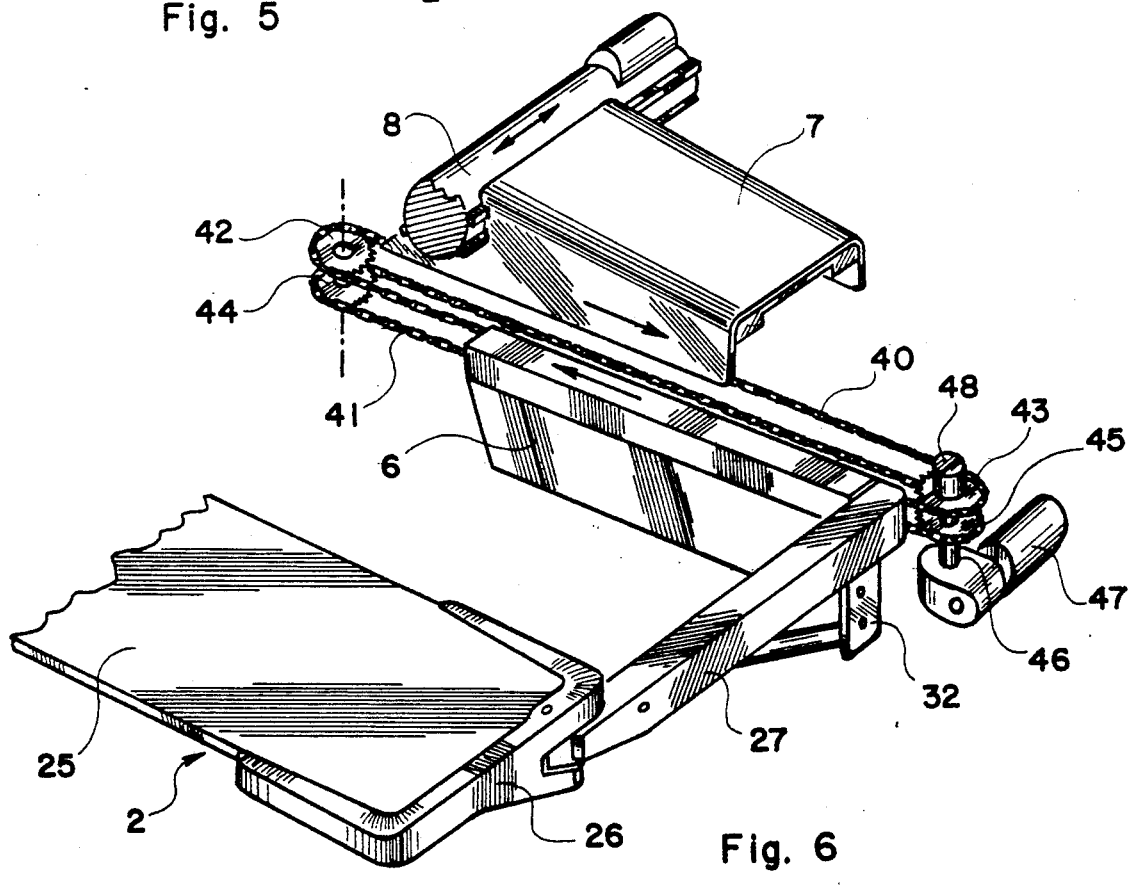
FIG. 6 illustrates the actuating means for the carriage means.

A drive means for carriage 6 and carriage 7 is shown in FIG. 6 and includes chains 40 and 41 extending parallelly over chain sprockets 42,43 and 44,45, respectively. Sprockets 44,45 are mounted on a shaft 46 connected to a motor drive 47 by an engaging means 48 for engaging chains 40 and 41 either individually or simultaneously so that both carriages move in unison toward or away from one another each traveling only a half of a distance required to cause a desired relative displacement of the radiation axis and the body.

In the alternative embodiment of this invention (FIG. 2) carriage assembly 3 is U-shaped and includes a section 50 extending in a direction parallel to the radiation axis which section is of a telescopic construction providing a relative movement therebetween and having a spot device 9 rotateably mounted thereon and rotateable around a longitudinal axis of elongated support member 8 (the second direction).

Table top may be swiveled in its support mounting 49 in its plane when in a horizontal position for easier loading of the patient onto the table top and for rotating the carriage assembly 180° to interchange a position of the image receptor with that of the X-ray source, one being above and the other being below the table top; a locking mechanism 51 including a solenoid and a plunger (not shown) being included to preclude said swiveling movement when the table top is in a tilted plane and also to preclude tilting of said table top when swiveled away.

What is claimed is:

1. An X-ray examination apparatus comprising in combination:
    a telescoping vertical support member extending from and supported by a base;
    a pivotable structure including a semicircular planar member disposed in a vertical plane and supported by said telescoping vertical support in a pivotable arrangement about an axis passing through the center of the radius of said semicircular planar member and parallel to a first horizontal direction, and wherein said semicircular planar member supports two parallel rail systems extending in a second horizontal direction generally parallel to said first horizontal direction;
    a first and a second support members mounted repectively on said parallel rail systems in a slidable arrangement in the second horizontal direction, and wherein said first and said second support members at their respective outwardly positions at least partly overhang opposite extremities of said semicircular planar member and wherein their respective ranges of travel extend at least partly into each other;
    a carriage for supporting an X-ray source and an X-ray image receptor supported by an elongated member disposed in the first horizontal direction and supported by the second support member in a slidable arrangement in said first horizontal direction;
    a patient table disposed intermediate said X-ray source and said X-ray image receptor and supported in an overhanging arrangement by a supporting structure secured to said first support member.

2. A system according to claim 1 further including a first actuating means for vertical displacement of said telescoping vertical support member and a second actuating means for pivoting movement of said pivotable structure, a computer control means for controlling said first and said second actuating means individually and in combination.

3. An apparatus according to claim 1 wherein said semicircular planar member at least in part has a timing belt disposed therealong and secured thereto, wherein said timing belt is engaged by at least one timing wheel driven by a drive member.

4. An apparatus according to claim 3 wherein said first actuating means includes a ball screw actuator.

5. An system according to claim 1 wherein said carriage is rotatably supported by said elongated member about an axis parallel to the longitudinal axis of said elongated member.

6. A combination as set forth in claim 5 wherein said X-ray image receptor includes a spot film device.

7. An X-ray table assembly comprising in combination:
    a patient table supported by an overhanging support structure extending from and secured to a support means, said overhanging support structure comprising: a bracket supporting said patient table, an elongated member with one extremity pivotably secured to said support means and the other extremity pivotably secured to said bracket; a first elongated actuator member with one extremity pivotably secured to said support means and the other extremity pivotable secured to said bracket, a second elongated actuator member with one extremity pivotably secured to said support means and the other extremity pivotably secured to said elongated member disposed in an angled relationship to said first elongated actuator member.

* * * * *